United States Patent [19]

Maurer et al.

[11] 4,418,073
[45] Nov. 29, 1983

[54] COMBATING PESTS WITH N-ACYLATED N-METHYL-CARBAMIC ACID O-PYRAZOL-4-YL ESTERS

[75] Inventors: Fritz Maurer, Wuppertal; Ingeborg Hammann, Cologne; Bernhard Homeyer, Leverkusen; Wolfgang Behrenz, Overath, all of Fed. Rep. of Germany

[73] Assignee: Bayer Aktiengesellschaft, Leverkusen, Fed. Rep. of Germany

[21] Appl. No.: 271,080

[22] Filed: Jun. 8, 1981

[30] Foreign Application Priority Data

Jun. 25, 1980 [DE] Fed. Rep. of Germany ....... 3023675

[51] Int. Cl.³ .................... A01N 43/56; C07D 231/18
[52] U.S. Cl. ............................... 424/273 P; 548/374; 548/375
[58] Field of Search .............................. 548/374, 375; 424/273 P

[56] References Cited

U.S. PATENT DOCUMENTS 3,857,860  12/1974  Kuhle et al. ................... 560/137
4,181,734  1/1980   D'Silva ........................ 424/285

FOREIGN PATENT DOCUMENTS 23326  2/1981  European Pat. Off. .

*Primary Examiner*—Henry R. Jiles
*Assistant Examiner*—Natalia Harkaway
*Attorney, Agent, or Firm*—Sprung, Horn, Kramer & Woods

[57] ABSTRACT

N-Acylated N-methyl-carbamic acid O-pyrazol-4-yl esters of the formula

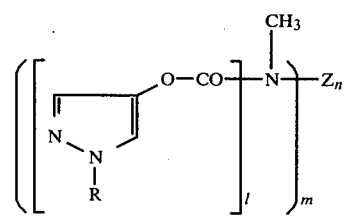

in which
R represents an optionally substituted alkyl, alkenyl, alkynyl, cycloalkyl, aralkyl or aryl radical,
Z represents an acyl radical,
l represents 1 or 2,
m represents 1 or 2 and
n represents zero or 1,
which possess pesticidal activity.

11 Claims, No Drawings

COMBATING PESTS WITH N-ACYLATED N-METHYL-CARBAMIC ACID O-PYRAZOL-4-YL ESTERS

The invention relates to certain new N-acylated N-methyl-carbamic acid O-pyrazol-4-yl esters, to a process for their preparation and to their use as agents for combating pests, in particular as insecticides, acaricides and nematicides.

It is known that certain N,N-dimethyl-carbamic acid O-pyrazolyl esters, for example N,N-dimethyl-carbamic acid O-(1-phenyl-3-methyl-pyrazol-5-yl) ester and O-(1-isopropyl-3-methyl-pyrazol-5-yl) ester, have insecticidal properties (see Swiss Patent Specification No. 282,655).

However, the insecticidal action of these compounds is not always satisfactory, especially in the case of low concentrations of active compound and when small amounts are applied.

The present invention now provides, as new compounds, the N-acylated N-methyl-carbamic acid O-pyrazol-4-yl esters of the general formula

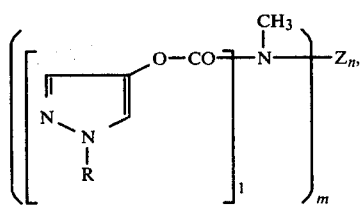   (I)

in which
R represents an optionally substituted radical selected from alkyl, alkenyl, alkynyl, cycloalkyl, aralkyl and aryl,
Z represents an acyl radical,
l represents 1 or 2,
m represents 1 or 2 and
n represents zero or 1.

By "an acyl radical", in this connection, there is to be understood the radical of one of the acids customary for forming derivatives of pesticidally active N-methyl-carbamic acid esters, or of a corresponding acid derivative, for example a carboxylic acid derivative, carbonic acid derivative or sulphenic acid derivative, sulphur dichloride and disulphur dichloride being included as the simplest sulphenic acid derivatives.

The invention also provides a process for the preparation of a compound of the formula (I) in which
(a) an N-methyl-carbamic acid O-pyrazol-4-yl ester of the general formula

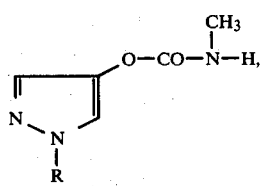   (II)

in which
R has the abovementioned meaning, is reacted with an acylating agent of the general formula $$X-Z_n$$   (III), in which
Z has the abovementioned meaning,
X represents fluorine, chlorine or bromine and
n represents 1, if appropriate in the presence of an acid acceptor and if appropriate using a diluent, or
(b) a 4-hydroxy-pyrazole of the general formula

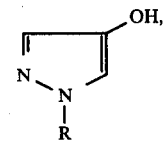   (IV)

in which
R has the abovementioned meaning, is reacted with an acylating agent of the general formula

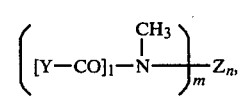   (V)

in which
Z, l, m and n have the abovementioned meanings and
Y represents fluorine or chlorine,
if appropriate in the presence of an acid acceptor, if appropriate using a diluent and if appropriate in the presence of another compound which can be carbamoylated.

The N-acylated N-methyl-carbamic acid O-pyrazol-4-yl esters of the formula (I) are distinguished by a powerful pesticidal activity.

Surprisingly, the compounds of the formula (I) exhibit a considerably more powerful insecticidal, acaricidal and nematicidal action than the compounds of analogous structure and the same type of action which are known from the state of the art.

The preferred compounds of the formula (I) include those in which
R represents $C_1$-$C_5$-alkyl which is optionally substituted by halogen, cyano, $C_1$-$C_4$-alkoxy or $C_1$-$C_4$-alkylthio, or represents $C_3$-$C_5$-alkenyl, $C_3$-$C_5$-alkynyl or $C_3$-$C_6$-cycloalkyl, or represents an optionally halogen-substituted phenyl, benzyl or phenylethyl radical,
and in which, in the case where l, m and n each represent 1,
Z represents the radical -CO-$R^1$, wherein
$R^1$ represents halogen, $C_1$-$C_4$-alkoxy, $C_3$-$C_5$-alkenoxy, $C_3$-$C_5$-alkynoxy, $C_1$-$C_4$-alkylthio, $C_1$-$C_4$-monoalkylamino, $C_1$-$C_4$-dialkyl-amino or $C_1$-$C_4$-alkyl-hydroxylamino, or represents a phenoxy, phenylthio or phenylamino radical which is optionally substituted by halogen, nitro, cyano, trifluoromethyl, $C_1$-$C_4$-alkyl, $C_1$-$C_4$-alkoxy, $C_1$-$C_4$-alkoxy, $C_1$-$C_4$-alkylenedioxy, $C_1$-$C_4$-alkylthio or $C_1$-$C_4$-alkoxy-carbonyl, or represents 2,3-dihydro-2,2-dimethyl-2-benzofuranyl, or represents the radical

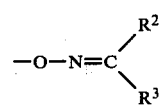

wherein
$R^2$ represents hydrogen, $C_1$-$C_4$-alkyl or di-($C_1$-$C_4$-alkyl)amino-carbonyl and $R^3$ represents $C_1$-$C_4$-alkyl, $C_1$-$C_4$-alkylthio, cyano-$C_1$-$C_4$-alkylthio or $C_1$-$C_4$-alkylthio-$C_1$-$C_4$-alkyl, or $R^2$ and $R^3$ together represent $C_2$-$C_8$-alkanediyl which is optionally interrupted by oxygen, sulphur, SO or $SO_2$, or in which, also in the case where l, m and n each represent 1, Z represents the radical -$S_r(O)_s$-$R^4$, wherein r represents 1 or 2, s represents zero, 1 or 2 and $R^4$ represents optionally halogen-substituted $C_1$-$C_4$-alkyl, $C_3$-$C_5$-alkenyl, $C_3$-$C_5$-alkynyl or $C_3$-$C_6$-cycloalkyl, or represents a phenyl, benzyl or phenylethyl radical which is optionally substituted by halogen, cyano, nitro, trifluoromethyl, $C_1$-$C_4$-alkyl or $C_1$-$C_4$-alkoxy, or represents the radical

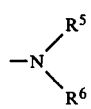

wherein $R^5$ represents $C_1$-$C_4$-alkyl, $C_3$-$C_5$-alkenyl, $C_3$-$C_5$-alkynyl, $C_3$-$C_6$-cycloalkyl or benzyl and $R^6$ represents $C_1$-$C_4$-alkyl, $C_3$-$C_5$-alkenyl, $C_3$-$C_5$-alkynyl, $C_3$-$C_6$-cycloalkyl, benzyl, phenylethyl, halogencarbonyl, formyl, $C_1$-$C_4$-alkyl-carbonyl, $C_1$-$C_4$-alkoxy-carbonyl, $C_1$-$C_4$-alkoxy-phenoxy-carbonyl, $C_3$-$C_5$-alkynoxy-carbonyl, $C_3$-$C_5$-alkenoxy-carbonyl, $C_1$-$C_4$-alkylthiocarbonyl, $C_1$-$C_4$-alkyl-amino-carbonyl, $C_1$-$C_4$-alkyl-hydroxylaminocarbonyl, $C_1$-$C_{10}$-alkyl-phenoxy-carbonyl, di-($C_1C_4$-alkyl)amino-carbonyl, phenylthiocarbonyl, phenoxy-carbonyl or 2,3-dihydro-2,2-dimethyl-7-benzofuranyloxycarbonyl, or represents a phenylsulphenyl, phenylsulphinyl, phenylsulphonyl or phenyl radical which is optionally substituted by halogen, cyano, nitro, trifluoromethyl, $C_1$-$C_{10}$-alkyl or $C_1$-$C_4$-alkoxy, or represents the radical

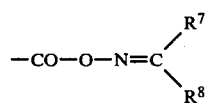

wherein $R^7$ has the meaning given above for $R^2$ and $R^8$ has the meaning give for $R^3$, or wherein, in the radical

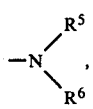

$R^5$ and $R^6$ together represent a hydrocarbon chain which has 3 to 8 carbon atoms and is optionally interrupted by oxygen or sulphur.

Further preferred compounds of the formula (I) are those in which

R has the meaning given above as preferred, and either l represents 2, m represents 1 and n represents zero, or, for the case where Z represents sulphur, l represents 1, m represents 2 and n represents 1.

If, for example, N-methyl-carbamic acid O-(1-methyl-pyrazol-4-yl) ester and trichloromethanesulphenic acid chloride are used as starting materials in process variant (a) and, for example, 1-methyl-4-hydroxypyrazole and bis-chlorocarbonylmethylamine are used as starting materials in process variant (b), the reactions which proceed can be outlined by the following equations:

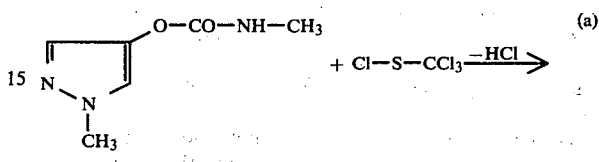

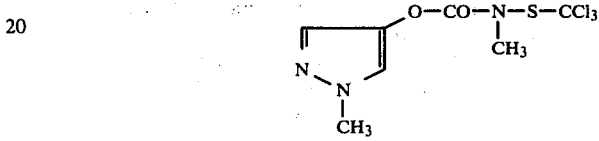

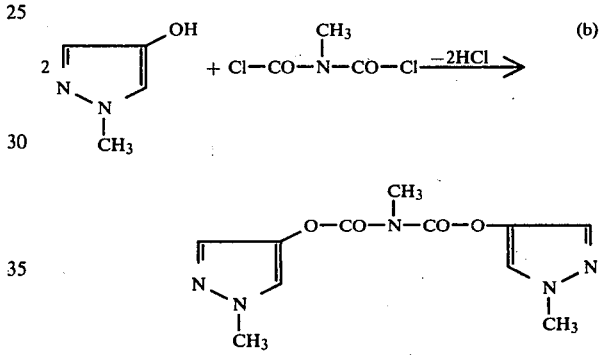

Formula (II) provides a definition of the N-methylcarbamic acid O-pyrazol-4-yl esters to be used as starting materials in process variant (a). Preferably, in this formula, R has the meaning given above as preferred in the definition of the radical R in the formula (I).

Examples of compounds of the formula (II) which may be mentioned are: N-methyl-carbamic acid 1-methyl-, 1-ethyl-, 1-n-propyl-, 1-iso-propyl-, 1-(1,1-dimethylpropyl)-, 1-(2,2-dimethylpropyl)-, 1-n-butyl-, 1-iso-butyl-, 1-sec.-butyl-, 1-tert.-butyl-, 1-(1-methylbutyl)-, 1-(2-methylbutyl)-, 1-(3-methylbutyl)-, 1-n-pentyl-, 1-(1-ethyl-propyl)-, 1-cyclopropyl-, 1-cyclobutyl-, 1-cyclopentyl-, 1-cyclohexyl-, 1-allyl-, 1-(3-methyl-2-butenyl)-, 1-propargyl-, 1-methylthio-methyl-, 1-(2-cyano-ethyl)-, 1-(2-methoxy-ethyl)-, 1-(2-ethoxy-ethyl)-, 1-(2-methylthio-ethyl)-, 1-chloromethyl-, 1-dichloromethyl-, 1-trichloromethyl-, 1-(2-chloro-ethyl)-, 1-trifluoromethyl-, 1-phenyl-, 1-benzyl- and 1-phenethylpyrazol-4-yl ester.

The compounds of the formula (II) are the subject of U.S. Ser. No. 167,556, filed July 11, 1980.

The compounds of the formula (II) are obtained by reacting 4-hydroxy-pyrazoles of the formula (IV) with methyl isocyanate in the presence of a diluent, for example acetone, and if appropriate in the presence of a catalyst, for example triethylamine, at temperatures between 10° and 80° C.

Formula (III) provides a definition of the acylating agents also to be used as starting substances in process variant (a). Preferably, in this formula, Z has the meaning given above as preferred in the definition of the radical Z in formula (I), and can furthermore represent sulphur, and, preferably, X represents fluorine or chlorine and n represents 1.

Examples of the compounds of the formula (III) which may be mentioned are: sulphur dichloride, disulphur dichloride, methanesulphenic acid chloride, trichloromethanesulphenic acid chloride, dimethylamino- or di-n-butyl-amino-sulphenic acid chloride and morpholinosulphenic acid chloride.

Compounds of the formula (III) are known (see DE-OS (German Published Specification) No. 2,433,680).

Formula (IV) provides a definition of the 4-hydroxy-pyrazoles to be used as starting substances in process variant (b). Preferably, in this formula, R has the meaning given above as preferred in the definition of the radical R in formula (I).

Examples of the compounds of the formula (IV) which may be mentioned are: 1-methyl-, 1-ethyl-, 1-n-propyl-, 1-iso-propyl-, 1-(1,1-dimethylpropyl)-, 1-(2,2-dimethylpropyl)-, 1-n-butyl-, 1-iso-butyl-, 1-sec.-butyl,-1-tert.-butyl-, 1-(1-methylbutyl)-, 1-(2-methylbutyl)-, 1-(3-methylbutyl)-, 1-m-pentyl-, 1-(1-ethyl-propyl)-, 1-cyclopropyl-, 1-cyclobutyl-, 1-cyclopentyl-, 1-cyclohexyl-, 1-allyl-, 1-(3-methyl-2-butenyl)-, 1-propargyl-, 1-methylthio-methyl-, 1-(2-cyano-ethyl), 1-(2-methoxy-ethyl)-, 1-(2-ethoxy-ethyl), 1-(2-methylthio-ethyl)-, 1-chloromethyl-, 1-dichloromethyl-, 1-trichloromethyl-, 1-(2-chloroethyl)-, 1-trifluoro-methyl-, 1-phenyl-, 1-benzyl- and 1-phenethyl-4-hydroxy-pyrazole.

4-Hydroxypyrazoles of the formula (IV) are known (see Liebigs Ann. Chem. 313 (1900), 17), and some of them are the subject of U.S. Ser. No. 167,556, filed July 11, 1980, supra.

The 4-hydroxy-pyrazoles are obtained, for example, by reacting the corresponding 4-methoxypyrazoles with hydrobromic acid. The 4-methoxy-pyrazoles can be prepared in a known manner, for example by reacting corresponding hydrazines with 2-methoxy-4-dimethylaminoacrolein (see Archiv der Pharmazie 300, (1967), 704–708).

Formula (V) provides a definition of the acylating agents also to be used as starting substances in process variant (b). Preferably, in this formula, Z has the meaning given above as preferred in the definition of the radical Z in formula (I), and can furthermore represent sulphur, and, preferably, Y represents fluorine or chlorine, l represents 1 or 2, m represents 1 or 2 and n represents zero or 1.

Examples of the compounds of the formula (V) which may be mentioned are: bis-chlorocarbonyl-methylamine, bis-(N-methyl-N-fluorocarbonylamino)-sulphide N-methyl-N-(1-methylthioacetaldehyde 0-(methylcarbamoyl-sulphenyl)oxime)-carbamoyl fluoride, N-methyl-N-trichloromethylsulphenyl-carbamoyl fluoride, N-methyl-N-chlorodifluoromethylsulphenyl-carbamoyl fluoride, N-methyl-N-fluorodichloromethylsulphenyl-carbamoyl fluoride, N-methyl-N-phenyl-sulphenyl-carbamoyl fluoride, N,N'-bis-fluorocarbonyl-dithio-bis-methylamine, N-methyl-N-methylthiosulphenyl-carbamoyl fluoride, N-methyl-N-(2-methyl-2-propylthio-sulphenyl)-carbamoyl fluoride, N-methyl-N-morpholinosulphenyl-carbamoyl fluoride, N-methyl-N-(N-methyl-N-formyl-amino-sulphenyl)-carbamoyl fluoride, N-methyl-N-(N-methyl-N-acetylaminosulphenyl)-carbamoyl fluoride and (N-methyl-N-(N'-fluorocarbonyl-N'-methyamino-sulphenyl)-carbamoyloxy-4-nonyl-benzene.

Compounds of the formula (V) are known DE-AS (German Published Specification) No. 1,297,095 and DE-OS (German Published Specifications) No. 2,425,211 and 2,530,278; DE-OS (German Published Specifications) No. 1,932,830, 2,530,278, 2,654,282 and 2,828,133; U.S. Ser. No. 819,021 filed July 25, 1977 and U.S. Pat. No. 4,181,734.

Compounds which can be carbamoylated and which are optionally employed in process variant (b) are, preferably, (a) phenols, thiophenols, phenylamines, hydroxypyrazoles and hydroxy-pyrimidines, which in each case optionally carry one or more substituents selected from halogen, cyano, nitro, $C_1$-$C_4$-alkyl-carbonyl, $C_1$-$C_4$-alkoxy-carbonyl, $C_1$-$C_4$-alkyl-amino-carbonyl, $C_1$-$C_4$-alkyl-amino and optionally halogen-substituted radicals from the series $C_1$-$C_5$-alkyl, $C_3$-$C_6$-cycloalkyl, $C_1$-$C_4$-alkoxy, $C_1$-$C_4$-alkylthio, $C_1$-$C_4$-alkylsulphinyl, $C_1$-$C_4$-alkyl-sulphonyl, $C_1$-$C_4$-alkoxy-$C_1$-$C_2$-alkyl, $C_1$-$C_4$-alkylthio-$C_1$-$C_2$-alkyl, $C_1$-$C_4$-alkylsulphinyl-$C_1$-$C_2$-alkyl, $C_1$-$C_4$-alkylsulphonyl-$C_1$-$C_2$-alkyl, $C_2$-$C_4$-alkanediyl, $C_2$-$C_4$-oxaalkanediyl and $C_1$-$C_4$-dioxaalkanediyl, (b) oximes of aldehydes with up to 8 carbon atoms, which optionally carry one or more substituents selected from halogen, cyano, dimethylcarbamoyl, $C_1$-$C_4$-alkylthio and $C_1$-$C_4$-alkylsulphonyl, or (c) aliphatic, saturated or unsaturated alcohols and amines with up to 6 carbon atoms.

Examples which may be mentioned of the compounds which can be carbamoylated are: thiophenol, 1-methylthio-acetaldehyde oxime, propargyl alcohol, phenol, dimethylamine, ethanol, allyl alcohol, 3,3-dimethylallyl alcohol, 2,3-dihydro-2,2-dimethyl-7-hydroxybenzofuran, 2-methylthio-isobutyraldehyde oxime, 2-isopropoxyphenol, ethylmercaptan, isopropyl alcohol, O,N-dimethylhydroxylamine, isopropylamine, 3-methyl-2-buten-1-ol, morpholine, 2-methyl-2-methylthio-propanaldoxime, 1-methylthio-1-dimethylaminocarbonyl-methanaldoxime, 3,3-dimethyl-1-methylthio-butan-2-one-oxime and 2,3-(dimethylmethylenedioxy)-phenol, and the compounds mentioned above as examples of 4-hydroxypyrazoles of the formula (IV).

Process variants (a) and (b) are preferably carried out using a diluent. Possible diluents are virtually any of the inert organic solvents. These include, as preferences, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene; ethers, such as diethyl ether, dibutyl ether, glycol dimethyl ether, diglycol dimethyl ether, tetrahydrofuran and dioxane; ketones, such as acetone, methyl ethyl ketone, methyl isopropyl ketone and methyl isobutyl ketone; esters, such as methyl acetate and ethyl acetate; nitriles, such as acetonitrile and propionitrile; amides, for example dimethylformamide, dimethylacetamide and N-methyl-pyrrolidone; and dimethylsulphoxide, tetramethylene sulphone and hexamethylphosphoric acid triamide.

Toluene is preferably used as the diluent.

Any of the customary acid-binding agents can be used as the acid acceptor. Acid-binding agents which have proved particularly suitable are alkali metal carbonates and alcoholates, such as sodium carbonate and potassium carbonate and sodium methylate or ethylate and potassium methylate or ethylate, and furthermore aliphatic, aromatic or heterocyclic amines, for example triethylamine, trimethylamine, dimethylaniline, dimethylbenzylamine, pyridine and diazabicycloundecene.

Triethylamine is preferably used as the acid acceptor.

The reaction temperature can be varied within a substantial range. In general, the reaction is carried out at between −20° and +100° C., preferably at from 0° to 80° C.

The processes according to the invention are in general carried out under normal pressure.

The starting materials are usually employed in equivalent amounts for carrying out the processes according to the invention. An excess of either of the reactants provides no substantial advantages. The reaction is in general carried out in a suitable diluent in the presence of an acid acceptor, and the reaction mixture is stirred at the required temperature for several hours. A water-immiscible organic solvent, for example toluene, is then added, if appropriate, and the organic phase is worked up in the customary manner, by washing, drying and distilling off the solvent.

Some of the compounds of the formula (I) are obtained in the form of oils, which in some cases cannot be distilled without decomposition, but can be freed from the last volatile constituents by so-called "incipient distillation", that is to say by prolonged heating to moderately elevated temperature under reduced pressure, and can be purified in this manner. They are characterized by their reflective index.

The active compounds are well tolerated by plants, have a favorable level of toxicity to warm-blooded animals, and are suitable for combating arthropod pests, especially insects and arachnids, and nematode pests, which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera spec.;* from the class of the Symphyla, for example *Scutigerella immaculata;* from the order of the Thysanura, for example *Lepisma saccharina;* from the order of the Collembola, for example *Onychiurus armatus;* from the order of the Orthoptera, for example Blatta orientalis, Periplaneta americana, Leucophaea maderae, Blattella germanica, Acheta domesticus, Gryllotalpa spp., Locusta migratoria migratorioides, Melanoplus differentialis and *Schistocerca gregaria;* from the order of the Dermaptera, for example Forficula auricularia;

from the order of the Isoptera, for example *Reticulitermes spp.;* from the order of the Anoplura, for example Phylloxera vastatrix, Pemphigus spp., Pediculus humanus corporis, Haematopinus spp. and *Linognathus spp.;* from the order of the Mallophaga, for example Trichodectes spp. and *Damalinea spp.;* from the order of the Thysanoptera, for example Hercinothrips femoralis and *Thrips tabaci;* from the order of the Heteroptera, for example *Eurygaster spp., Dysdercus intermedius, Piesma quadrata, Cimex lectularius, Rhodnius prolixus* and *Triatoma spp.;* from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus supp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp.* and *Psylla spp.;* from the order of the Lepidoptera, for example *Pectinophora gossypiella, Bupalus piniarius, Cheimatobia brumata, Lithiocolletis blancardella, Hyponomeuta padella, Plutella maculipennis, Malacosoma neustria, Euproctis chrysorrhoea, Lymantria spp., Bucculatrix thurberiella, Phyllocnistis citrella, Agrotis spp., Euxoa spp., Feltia spp., Earias insulana, Heliothis spp., Laphygma exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus supp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis* and *Costelytra zealandica;* from the order of the Hymenoptera, for example *Diprion spp., Hoplocampa spp., Lasius spp., Monomorium pharaonis* and *Vespa spp.;* from the order of the Diptera, for example *Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibic hortulanus, Oscinella frit, Phorbia spp., Pegomyia hyoscyami, Ceratitis capitata, Dacus oleae* and *Tipula paludosa;* from the order of the Siphonaptera, for example *Xenopsylla cheopis* and *Ceratophyllus spp.;* from the class of the Arachnida, for example *Scorpio maurus* and *Latrodectus mactans;* from the order of the Acarina, for example *Acarus siro, Argas spp., Ornithrodoros spp., Dermanyssus gallinae, Eriophyes ribis, Phyllocoptruta oleivora, Boophilus spp., Rhipicephalus spp., Amblyomma spp., Hyalomma spp.,*

*Ixodes spp., Psoroptes spp., Chorioptes spp., Sarcoptes spp., Tarsonemus spp., Bryobia praetiosa, Panonychus spp.* and *Tetranychus spp.*

The plant-parasitic nematodes include *Pratylenchus spp., Radopholus similis, Ditylenchus dipsaci, Tylenchulus semipenetrans, Heterodera spp., Meloidogyne spp., Aphelenchoides spp., Longidorus spp., Xiphinema spp.,* and *Trichodorus spp.*

The active compounds can be converted into the customary formulations, such as solutions, emulsions, suspensions, powders, dusting agents, foams, pastes, soluble powders, granules, aerosols, suspension-emulsion concentrates, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methyl-cellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal-phthalocyanine dyestuffs, and trace nutrients such as salts of iron, manganese, boron, copper, cobalt, molybdenum and zinc.

The formulations in general contain from 0.1 to 95 percent by weight of active compound, preferably between 0.5 and 90%.

The active compounds according to the invention can be present in their formulations of the types that are commercially available and in use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by micro-organisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 100% by weight of active compound, preferably between 0.0001 and 1% by weight.

The compounds are employed in a customary manner appropriate for the use forms.

When used against pests harmful to health and pests of stored products, the active compounds are distinguished by an excellent residual action on wood and clay as well as a good stability to alkali on limed substrates.

The present compounds are also suitable for combating ectoparasites and endoparasites in the field of veterinary medicine. The compounds may be used in a known manner in the veterinary sector, such as by oral administration, for example in the form of tablets, capsules, drinks and granules, by dermal application, for example by dipping, spraying, pouring on, spotting on and dusting, and by parenteral administration, for example in the form of an injection.

The invention also provides a pesticidal composition containing as active ingredient a compound of the invention in admixture with a solid or liquefied gaseous diluent or carrier or in admixture with a liquid diluent or carrier containing a surface-active agent.

The invention also provides a method of combating pests which comprises applying to the pests, or to a habitat thereof, a compound of the invention alone or in the form of a composition containing as active ingredient such a compound in admixture with a diluent or carrier.

The invention also provides a method of freeing or protecting domesticated animals from parasites which comprises applying to said animals a compound of the invention, in admixture with a diluent or carrier.

The invention also provides crops protected from damage by pests by being grown in areas in which immediately prior to and/or during the time of the growing a compound of the invention was applied, alone or in admixture with a diluent or carrier.

It will be seen that the usual methods of providing a harvested crop may be improved by the present invention.

The present invention further provides domesticated animals whenever freed or protected from parasites by the application to said animals of a compound according to the present invention, in admixture with a diluent or carrier.

PREPARATIVE EXAMPLES

EXAMPLE 1:

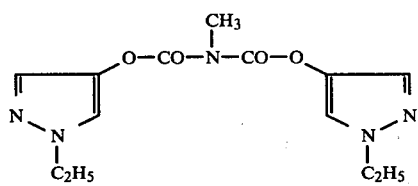

5.1 g (0.05 mol) of triethylamine were added dropwise to a mixture of 5.6 g (0.05 mol) of 1-ethyl-4-hydroxypyrazole, 3.9 g (0.025 mol) of bis-chlorocarbonylmethylamine and 100 ml of toluene. After 10 hours, the mixture was washed twice with 25 ml of water. The organic phase was dried over sodium sulphate and the solvent was then distilled off in vacuo. The residue was subjected to incipient distillation under a high vacuum. 7 g (91% of theory) of bis-[1-ethyl-pyrazol-4-yl-oxy]-carbonylmethylamine were obtained in this manner in the form of a light-brown oil with a refractive index $n_D^{20}$ of 1.5009.

EXAMPLE 2:

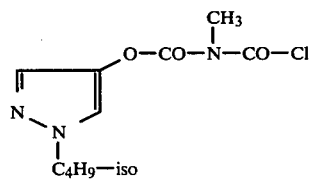

5.1 g (0.05 mol) of triethylamine were added to a solution of 7 g (0.05 mol) of 1-iso-butyl-4-hydroxypyrazole and 7.8 g (0.05 mol) of bis-chlorocarbonylmethylamine in 100 ml of toluene and the mixture was stirred at room temperature for 8 hours. The amine salt which had precipitated was then filtered off and rinsed with toluene and the filtrate was evaporated. 10 g (77% of theory) of N-chlorocarbonyl-N-[1-isobutylpyrazol-4-yl-oxy]-carbonyl-methylamine remained in the form of a light-brown oil with a refractive index $n_D^{24}$ of 1.5043.

EXAMPLE 3

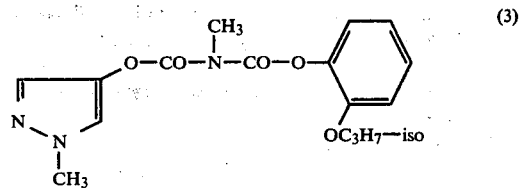

4.1 g (0.04 mol) of triethylamine were added dropwise to a solution of 4 g (0.04 mol) of 1-methyl-4-hydroxypyrazole and 6.25 g (0.04 mol) of bis-chlorocarbonylmethylamine in 100 ml of toluene and the mixture was subsequently stirred at room temperature for 4 hours. 6.1 g (0.04 mol) of 2-isopropoxyphenol and a further 4.1 g (0.04 mol) of triethylamine were then added and the mixture was subsequently stirred for 4 hours. The reaction mixture was then washed twice with 25 ml of water each time, the organic phase was dried over sodium sulphate and the solvent was distilled off in vacuo. The residue was subjected to incipient distillation under a high vacuum. 12.5 g (94% of theory) of N-[(2-isopropoxy)-phenoxy]-carbonyl-N-[1-methyl-pyrazol-4-yl-oxy]carbonyl-methylamine were thus obtained in the form of a yellow oil with a refractive index $n_D^{24}$ of 1.5271.

EXAMPLE 4:

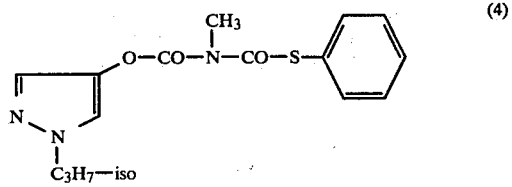

4. g (0.04 mol) of triethylamine were added dropwise to a solution of 9.8 g (0.04 mol) of N-chlorocarbonyl-N-[1-iso-propyl-pyrazol-4-yl-oxy]-carbonyl-methylamine—which had been prepared analogously to Example 2—and 4.4 g (0.04 mol) of thiophenol in 100 ml of toluene. The mixture was subsequently stirred at room temperature for 4 hours and was then extracted twice by shaking with 25 ml of water each time. The organic phase was dried over sodium sulphate and evaporated in vacuo. The residue was subjected to incipient distillation under a high vacuum. 12 g (94% of theory) of N-phenylthiocarbonyl-N-[1-isopropyl-pyrazol-4-yl-oxy]-carbonyl-methylamine were thus obtained as a brown oil with a refractive index $n_D^{20}$ of 1.5662.

The following compounds of the general formula

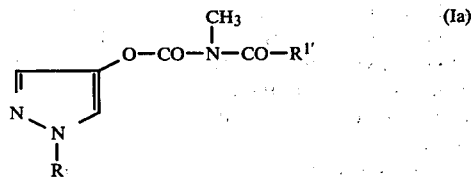

are obtained analogously to one of Examples 1 to 4:

| Compound Number | R | R¹' | Yield (% of theory) | Physical data (Refractive index; melting point °C.) |
|---|---|---|---|---|
| (5) | CH₃ | -O-N=C(CH₃)(SCH₃) | | |
| (6) | C₃H₇—iso | -O-CH=CH-N(N=)-C₃H₇—iso (pyrazole) | 84 | $n_D^{20}$: 1.5089 |
| (7) | C₄H₉—n | -O-CH=CH-N(N=)-C₄H₉—n (pyrazole) | 77 | $n_D^{20}$: 1.5055 |
| (8) | C₃H₇—iso | Cl | 98 | $n_D^{20}$: 1.5077 |
| (9) | C₃H₇—iso | -O-CH₂-C≡CH | 91 | $n_D^{23}$: 1.5004 |
| (10) | C₄H₉—iso | -O-CH=CH-N(N=)-C₄H₉—iso (pyrazole) | 77 | $n_D^{20}$: 1.5078 |
| (11) | C₃H₇—iso | -O-C₆H₅ | 91 | $n_D^{20}$: 1.5325 |
| (12) | CH₂=CH-CH₂ | -N(CH₃)₂ | | |
| (13) | C₄H₉—tert. | -N(CH₃)₂ | | |
| (14) | C₃H₇—iso | -OC₂H₅ | 98 | $n_D^{20}$: 1.4680 |
| (15) | CH≡C-CH₂ | -O-CH₂-CH=CH₂ | | |
| (16) | CH₃-S-CH₂ | -O-CH=CH-N(N=)-CH₂-SCH₃ (pyrazole) | | |
| (17) | C₃H₇—iso | -N(CH₃)₂ | 87 | $n_D^{20}$: 1.5011 |
| (18) | C₄H₉—sec. | -O-CH=CH-N(N=)-C₄H₉—sec. (pyrazole) | 77 | $n_D^{20}$: 1.5001 |
| (19) | C₄H₉—tert. | -O-CH₂-C≡CH | | |
| (20) | C₃H₇—iso | -O-N=C(CH₃)(SCH₃) | | $n_D^{20}$: 1.5047 |
| (21) | C₂H₅ | -O-N=C(CH₃)(SCH₃) | | |
| (22) | C₃H₇—iso | -O-CH₂-CH=CH₂ | 84 | $n_D^{20}$: 1.4953 |
| (23) | cyclopentyl | -O-CH=CH-N(N=)-cyclopentyl (pyrazole) | | |

-continued

| Compound Number | R | R¹' | Yield (% of theory) | Physical data (Refractive index; melting point °C.) |
|---|---|---|---|---|
| (24) | $CH_3$ | 2,2-dimethyl-2,3-dihydrobenzofuran-7-yloxy | | |
| (25) | $C_3H_7$—iso | $-O-N=C(CH_3)(SCH_3)$ | 80 | $n_D^{23}$: 1.5304 |
| (26) | $C_2H_5O-CH_2-CH_2$ | 4,5-dihydro-oxadiazin-N-($CH_2-CH_2-OC_2H_5$) | | |
| (27) | $C_4H_9$—sec. | $-O-N=CH-C(CH_3)_2-SCH_3$ | | |
| (28) | $CH(C_2H_5)_2$ | 4,5-dihydro-oxadiazin-N-$CH(C_2H_5)_2$ | | |
| (29) | $C_3H_7$—iso | 2-isopropoxyphenoxy | 83 | $n_D^{23}$: 1.5181 |
| (30) | cyclopropyl | 4,5-dihydro-oxadiazin-N-cyclopropyl | | |
| (31) | $C_3H_7$—iso | $-SC_2H_5$ | 83 | $n_D^{23}$: 1.5215 |
| (32) | $C_4H_9$—tert. | $-S-C_6H_5$ | | |
| (33) | $C_3H_7$—iso | $-OC_3H_7$—iso | 93 | $n_D^{23}$: 1.4930 |
| (34) | $C_2H_5$ | 2,2-dimethyl-2,3-dihydrobenzofuran-7-yloxy | | |
| (35) | $CH_3-S-CH_2$ | $-O-N=C(CH_3)(SCH_3)$ | | |

-continued

| Compound Number | R | R¹' | Yield (% of theory) | Physical data (Refractive index; melting point °C.) |
|---|---|---|---|---|
| (36) | $C_3H_7$—iso | ![structure: -O-phenyl with -O-C(CH_3)_2-CH_2- fused ring] | 87 | $n_D^{23}$: 1.5312 |
| (37) | $C_4H_9$—tert. | ![same type structure] | 86 | $n_D^{24}$: 1.5264 |
| (38) | $C_3H_7$—n | ![same type structure] | | |
| (39) | $C_3H_7$—iso | —N(OCH_3)(CH_3) | 83 | $n_D^{20}$: 1.4958 |
| (40) | $C_4H_9$—tert. | —O—[pyrazolyl]—N—$C_4H_9$—tert. | 77 | $n_D^{23}$: 1.5089 |
| (41) | $CH_3$ | —$CH_2$—CH=$CH_2$ | | |
| (42) | $C_2H_5$ | —NH—$C_3H_7$—iso | | |
| (43) | $C_4H_9$—sec. | —NH—$C_3H_7$—iso | | |
| (44) | $C_4H_9$—tert. | Cl | 88 | $n_D^{20}$ = 1.5057 |
| (45) | $C_4H_9$—tert. | —O—$CH_2$—CH=$C(CH_3)_2$ | | |
| (46) | $C_4H_9$—sec. | —O—N=C(CH_3)(SCH_3) | | |
| (47) | $C_4H_9$—tert. | —O—N=C(CH_3)(SCH_3) | | |
| (48) | $C_3H_7$—iso | —O—$CH_2$—CH=$C(CH_3)_2$ | 81 | $n_D^{25}$: 1.4949 |
| (49) | $C_3H_7$—iso | —NH—$C_3H_7$—iso | 97 | $n_D^{23}$: 1.4906 |
| (49a) | $C_3H_7$—iso | $CH_3$ | 88 | $n_D^{18}$: 1.4957 |
| (49b) | $C_4H_9$—sec. | $CH_3$ | 84 | $n_D^{25}$: 1.4889 |

EXAMPLE 5

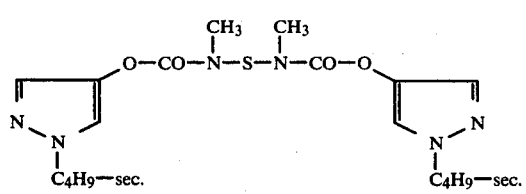

(50)

6.2 g (0.06 mol) of triethylamine were added dropwise to a mixture of 8.4 g (0.06 mol) of 1-sec.-butyl-4-hydroxy-pyrazole, 80 ml of toluene and 5.5 g (0.03 mol) of bis-(N-methyl-N-fluorocarbonylamino) sulphide at 20°–25° C. and the mixture was then subsequently stirred at room temperature for 10 hours. It was then extracted twice by shaking with 25 ml of water each time, the organic phase was dried over sodium sulphate and the solvent was distilled off in vacuo. 10 g (79% of theory) of bis-[N-methyl-N-(1-sec.-butyl-pyrazol-4-yloxy)-carbonylamino]sulphide remained in the form of a yellow oil with a refractive index $n_D^{19}$ of 1.5233.

EXAMPLE 6

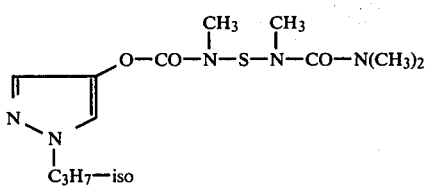

A mixture of 6.3 g (0.05 mol) of 1-isopropyl-4-hydroxy-pyrazole, 5.1 g (0.05 mol) of triethylamine and 200 ml of toluene was added to a solution of 9.2 g (0.05 mol) of bis-(N-methyl-N-fluorocarbonylamino) sulphide in 50 ml of toluene at 0°–5° C. The reaction mixture was subsequently stirred at room temperature for 2 hours, and 11 g of an approximately 45% strength aqueous dimethylamine solution were then added at 15°–20° C. The mixture was subsequently stirred at room temperature for 3 hours, the aqueous phase was separated off and the toluene solution was extracted twice more by shaking with 25 ml of water each time. The organic phase was dried over sodium sulphate and evaporated in vacuo. The residue was subjected to incipient distillation under a high vacuum. 13.5 g (86% of theory) of N-methyl-N-(N-dimethylaminocarbonyl-N-methyl-amino-sulphenyl)-carbamic acid O-(1-isopropyl-pyrazol-4-yl) ester were thus obtained in the form of a light-brown oil with a refractive index $n_D^{22}$ of 1.5192.

EXAMPLE 7

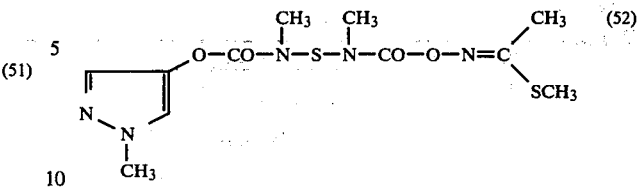

A solution of 2.5 g (0.025 mol) of triethylamine in 10 ml of toluene was added dropwise to a mixture of 6.7 g (0.025 mol) of N-methyl-N-[1-methylthio-acetaldehyde(O-methylcarbamoylsulphenyl)-oxime]-carbamoyl fluoride (for the preparation, see DOS (German Published Specification) No. 2,824,394), 2.5 g (0.025 mol) of 1-methyl-4-hydroxypyrazole and 50 ml of toluene. The mixture was subsequently stirred at room temperature for 24 hours and was extracted twice by shaking with 25 ml of water each time, and the organic phase was dried over sodium sulphate. The solvent was then distilled off in vacuo. 6 g (69% of theory) of N-methyl-N-[1-methylthioacetaldehyde(O-methylcarbamoylsulphenyl)-oxime]-carbamic acid O-(1-methyl-pyrazol-4-yl) ester were obtained in this manner in the form of yellow crystals with a melting point of 87° C.

The following compounds of the general formula

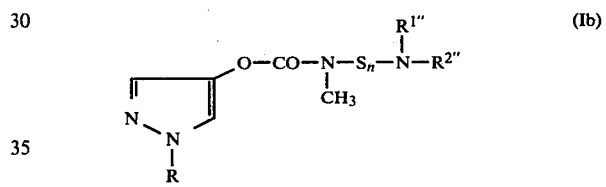

could be prepared analogously to one of Examples 5–7:

| Compound Number | R | $R^{1''}$ | $R^{2''}$ | n | Yield (% of theory) | Physical data (Refractive index; melting point °C.) |
|---|---|---|---|---|---|---|
| (53) | $C_4H_9$—tert. | | —$CH_2$—$CH_2$—O—$CH_2$—$CH_2$— | 1 | 57 | $n_D^{26}$: 1.5218 |
| (54) | $C_2H_5$ | $CH_3$ | —CO—$N(CH_3)_2$ | 1 | | |
| (55) | $C_3H_7$—iso | $CH_3$ | —CO—$OCH_3$ | 1 | 66 | $n_D^{18}$: 1.5427 |
| (56) | $CH_3$ | $CH_3$ | ![structure with -CO-O- linked to pyrazole N—$CH_3$] | 1 | | |
| (57) | $C_3H_7$—iso | $CH_3$ | ![structure with -CO-O- linked to pyrazole N—$C_3H_7$—iso] | 1 | 70 | 65–67 |
| (58) | $CH_2$=CH—$CH_2$ | $CH_3$ | ![structure with -CO-O- linked to pyrazole N—$CH_2$—CH=$CH_2$] | 1 | | |
| (59) | $C_3H_7$—iso | $C_4H_9$—n | —$C_4H_9$—n | 1 | | |
| (60) | $C_4H_9$—sec. | $CH_3$ | —$CH_3$ | 1 | | |
| (61) | $C_3H_7$—iso | $CH_3$ | —CO—O—$CH_2$—CH=$CH_2$ | 1 | 84 | $n_D^{22}$: 1.5098 |

-continued

| Compound Number | R | R$^{1''}$ | R$^{2''}$ | n | Yield (% of theory) | Physical data (Refractive index; melting point °C.) |
|---|---|---|---|---|---|---|
| (62) | C$_2$H$_5$ | CH$_3$ | —CO—O—N=C(CH$_3$)(SCH$_3$) | 1 | | |
| (63) | C$_3$H$_7$—iso | CH$_3$ | —CO—O—N=C(CH$_3$)(SCH$_3$) | 1 | 96 | n$_D^{20}$: 1.5405 |
| (64) | cyclopentyl | CH$_3$ | —CO—O—(pyrazolyl)—N-cyclopentyl | 1 | | |
| (65) | CH$_3$—S—CH$_2$ | CH$_3$ | —CO—O—(pyrazolyl)—N—CH$_2$—S—CH$_3$ | 1 | | |
| (66) | C$_3$H$_7$—iso | CH$_3$ | —CO—OC$_3$H$_7$—iso | 1 | | |
| (67) | C$_4$H$_9$—tert. | CH$_3$ | —CO—O—(pyrazolyl)—N—C$_4$H$_9$—tert. | 1 | 63 | 60–62 |
| (68) | cyclopropyl | CH$_3$ | —CO—O—(pyrazolyl)—N-cyclopropyl | 1 | | |
| (69) | C$_3$H$_7$n | CH$_3$ | —CO—O—N=C(CH$_3$)(SCH$_3$) | 1 | | |
| (70) | C$_3$H$_7$—iso | CH$_3$ | —CO—SC$_2$H$_5$ | 1 | 83 | n$_D^{22}$: 1.5288 |
| (71) | C$_3$H$_7$—iso | CH$_3$ | —CH$_2$—CH$_2$—O—CH$_2$—CH$_2$— | 1 | 60 | n$_D^{26}$: 1.5223 |
| (72) | CH≡C—CH$_2$ | CH$_3$ | —CO—O—(pyrazolyl)—N—CH$_2$—C≡CH | 1 | | |
| (73) | C$_4$H$_9$—sec. | CH$_3$ | —CO—N(CH$_3$)$_2$ | 1 | | |
| (74) | CH$_3$—S—CH$_2$ | C$_4$H$_9$—n | —C$_4$H$_9$—n | 1 | | |
| (75) | C$_3$H$_7$—iso | CH$_3$ | —CO—O—C$_6$H$_5$ | 1 | 93 | n$_D^{22}$: 1.5320 |
| (76) | C(CH$_3$)$_2$—CH$_2$—CH$_3$ | CH$_3$ | —CO—O—(pyrazolyl)—N—C(CH$_3$)$_2$—CH$_2$—CH$_3$ | 1 | 97 | n$_D^{23}$: 1.5112 |
| (77) | C$_4$H$_9$—tert. | CH$_3$ | —CO—F | 1 | 95 | n$_D^{24}$: 1.5037 |
| (78) | NC—CH$_2$—CH$_2$ | CH$_3$ | —CO—O—(pyrazolyl)—N—CH$_2$—CH$_2$—CN | 1 | | |

-continued

| Compound Number | R | R[1″] | R[2″] | n | Yield (% of theory) | Physical data (Refractive index; melting point °C.) |
|---|---|---|---|---|---|---|
| (79) | $C_3H_7$—iso | $CH_3$ | —CO—S—C₆H₅ (phenyl) | 1 | 85 | $n_D^{22}$: 1.5767 |
| (80) | $C_4H_9$—n | $CH_3$ | —CO—O—N=C(CH₃)(SCH₃) | 1 | | |
| (81) | $C_4H_9$—tert. | $CH_3$ | —CO—O—CH₂—C≡CH | 1 | 88 | $n_D^{23}$: 1.5121 |
| (82) | $C_2H_5$ | $CH_3$ | —CO—O-(3-(2,2-dimethyl-benzofuran)) | 1 | | |
| (83) | $C_3H_7$—iso | $CH_3$ | —CO—O-(2-iso-propoxyphenyl) | 1 | 89 | $n_D^{22}$: 1.5198 |
| (84) | $C_2H_5O$—$CH_2$—$CH_2$ | $CH_3$ | —CO—O—N(CH₂—CH₂—OC₂H₅)—N=CH— | 1 | | |
| (85) | $C_3H_7$—iso | $CH_3$ | —CO—O-(3-(2,2-dimethyl-benzofuran)) | 1 | 98 | $n_D^{22}$: 1.5111 |
| (86) | $C_4H_9$—sec. | $C_4H_9$—n | —$C_4H_9$—n | 1 | | |
| (87) | $C_4H_9$—iso | $C_4H_9$—n | —$C_4H_9$—n | 1 | | |
| (88) | $C_3H_7$—iso | $CH_3$ | —CO—O—N=C(CH₃)(CH₃) | 1 | 87 | $n_D^{23}$: 1.5179 |
| (89) | $C_4H_9$—tert. | $CH_3$ | —CO—N(CH₃)₂ | 1 | | |
| (90) | $C_3H_7$—iso | $CH_3$ | —CO—N(CH₃)(OCH₃) | 1 | 83 | $n_D^{23}$: 1.5123 |
| (91) | $CH(C_2H_5)_2$ | $CH_3$ | —CO—O—N=C(CH₃)(SCH₃) | 1 | | |
| (92) | $C_3H_7$—iso | $CH_3$ | —CO—F | 1 | 95 | $n_D^{24}$: 1.5059 |
| (93) | $C_4H_9$—tert. | $CH_3$ | —CO—O—N=C(CH₃)(SCH₃) | 1 | 92 | $n_D^{20}$: 1.5350 |

-continued

| Compound Number | R | R¹'' | R²'' | n | Yield (% of theory) | Physical data (Refractive index; melting point °C.) |
|---|---|---|---|---|---|---|
| (94) | C₃H₇—iso | CH₃ | —CO—O—N=CH—C(CH₃)₂—SCH₃ | 1 | | |
| (95) | CH₂—C(CH₃)₃ | CH₃ | —COO-(pyrazole)-N—CH₂—C(CH₃)₃ | 1 | | |
| (96) | C₃H₇—iso | CH₃ | —CO—O-(pyrazole)-N—C₃H₇—iso | 2 | 94 | $n_D^{19}$: 1.5389 |
| (97) | C₄H₉—tert | CH₃ | —CO—O-(pyrazole)-N—C₄H₉tert | 2 | 88 | $n_D^{19}$: 1.5308 |
| (98) | C₃H₇—iso | CH₃ | —CO—F | 2 | 93 | $n_D^{19}$: 1.5297 |
| (99) | CH₂—CH₂—Br | CH₃ | —CO—F | 1 | 85 | $n_D^{22}$: 1.5320 |
| (100) | C(CH₃)₂C₂H₅ | CH₃ | —CO—O-(pyrazole)-N—C(CH₃)₂C₂H₅ | 2 | 91 | $n_D^{22}$: 1.5250 |
| (101) | C₃H₇—iso | CH₃ | —CO—O—CH₂—C≡CH | 1 | 84 | $n_D^{23}$: 1.5139 |
| (102) | C₄H₉—sec. | CH₃ | —CO—NH—C₃H₇—iso | 1 | | |
| (103) | C₃H₇—iso | CH₃ | —CO—NH—C₃H₇—iso | 1 | 84 | $n_D^{23}$: 1.5111 |
| (104) | C₄H₉—tert. | CH₃ | —CO—O—CH₂—CH=C(CH₃)₂ | 1 | | |
| (105) | C₃H₇—iso | CH₃ | —CO—O—CH₂—CH=C(CH₃)₂ | 1 | 84 | $n_D^{25}$: 1.5061 |
| (106) | C₃H₇—iso | CH₃ | —CO—OC₂H₅ | 1 | 87 | $n_D^{23}$: 1.5048 |
| (107) | C₄H₉—tert. | CH₃ | —CO—O—CH₂—CH=CH₂ | 1 | 80 | $n_D^{23}$: 1.5071 |
| (108) | C₃H₇—iso | CH₃ | —CO—O—(C₆H₄)—C₄H₉—tert. | 1 | 83 | $n_D^{27}$: 1.5262 |
| (109) | C₃H₇—iso | CH₃ | —CO—O—(C₆H₄)—C₃H₇—iso | 1 | 98 | $n_D^{27}$: 1.5279 |
| (110) | C₃H₇—iso | CH₃ | —CO—O—(C₆H₄)—C₉H₁₉ | 1 | 97 | $n_D^{26}$: 1.5182 |
| (111) | C₄H₉—tert | CH₃ | —COO—(C₆H₅) | 1 | 93 | $n_D^{20}$: 1.5320 |
| (112) | C₄H₉—tert | CH₃ | —CO—NH—C₃H₇—iso | 1 | 80 | $n_D^{20}$: 1.5119 |
| (113) | C₄H₉—tert | CH₃ | —CO—N(OCH₃)(CH₃) | 1 | 87 | $n_D^{20}$: 1.5123 |

-continued

| Compound Number | R | R$^{1''}$ | R$^{2''}$ | n | Yield (% of theory) | Physical data (Refractive index; melting point °C.) |
|---|---|---|---|---|---|---|
| (114) | CH$_2$CH$_2$Br | CH$_3$ | −CO−O−C(=N-N(CH$_2$CH$_2$Br)−CH=) (pyrazolyl) | 1 | 76 | n$_D^{23}$: 1.5336 |
| (115) | C$_3$H$_7$—iso | CH$_3$ | −SO$_2$−C$_6$H$_4$−CH$_3$ | 1 | 88 | n$_D^{22}$: 1.5561 |
| (116) | C$_4$H$_9$—tert | CH$_3$ | −SO$_2$−C$_6$H$_4$−CH$_3$ | 1 | 85 | n$_D^{22}$: 1.5509 |
| (117) | C$_4$H$_9$—sec | CH$_3$ | −SO$_2$−C$_6$H$_4$−CH$_3$ | 1 | 91 | n$_D^{22}$: 1.5508 |
| (117a) | C$_3$H$_7$n | CH$_3$ | −CO−O−(1-n-propylpyrazol-4-yl) | 1 | 82 | n$_D^{18}$: 1.5275 |
| (117b) | C$_4$H$_9$—n | CH$_3$ | −CO−O−(1-n-butylpyrazol-4-yl) | 1 | 88 | n$_D^{18}$: 1.5218 |
| (117c) | C$_2$H$_5$ | CH$_3$ | −CO−O−(1-ethylpyrazol-4-yl) | 1 | 88 | 62 |

EXAMPLE 8

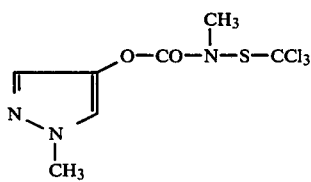

(162)

5.1 g (0.05 mol) of triethylamine were added dropwise to a mixture of 11.3 g (0.05 mol) of N-methyl-N-trichloromethylthio-carbamoyl fluoride, 4.9 g (0.05 mol) of 1-methyl-4-hydroxypyrazole and 150 ml of toluene. After 4 hours, the mixture was extracted twice with 25 ml of water each time. The organic phase was dried over sodium sulphate and evaporated in vacuo. The residue was subjected to incipient distillation under a high vacuum. 12.5 g (82% of theory) of N-methyl-N-trichloromethylthiocarbamic acid O-(1-methyl-pyrazol-4-yl) ester were thus obtained in the form of a yellow oil with a refractive index n$_D^{23}$ of 1.5492.

The following compounds of the general formula

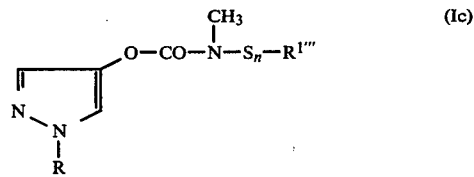

(Ic)

could be prepared analogously to Example 8:

| Compound Number | R | R$^{1'''}$ | n | Yield (% of theory) | Refractive index; melting point °C. |
|---|---|---|---|---|---|
| (118) | C$_3$H$_7$—iso | CCl$_2$F | 1 | 89 | n$_D^{18}$:1.5122 |
| (119) | C$_4$H$_9$—tert. | CCl$_3$ | 1 | 92 | 56 |
| (120) | C$_4$H$_9$—tert. | CCl$_2$F | 1 | 85 | n$_D^{18}$:1.5108 |
| (121) | C$_3$H$_7$—iso | CH$_3$ | 1 | | |
| (122) | C$_3$H$_7$—iso | C$_6$H$_5$ | 1 | | |

-continued

| Compound Number | R | R¹''' | n | Yield (% of theory) | Refractive index; melting point °C. |
|---|---|---|---|---|---|
| (123) | $C_3H_7$—iso | $CH_2$—CH=$CH_2$ | 1 | | |
| (124) | $C_4H_9$—iso | $CCl_3$ | 1 | | |
| (125) | $C_4H_9$—iso | $CCl_2F$ | 1 | 91 | $n_D^{28}$:1.5051 |
| (126) | $C_4H_9$—sec. | $CCl_3$ | 1 | 92 | $n_D^{25}$:1.5283 |
| (127) | $C_4H_9$—sec. | $CCl_2F$ | 1 | 61 | $n_D^{19}$:1.5092 |
| (128) | $C_3H_7$—iso | $CCl_3$ | 1 | 79 | $n_D^{21}$:1.5378 |
| (129) | $C_2H_5$ | $CCl_3$ | 1 | 94 | $n_D^{26}$:1.5392 |
| (130) | $C_4H_9$—sec. | $CH_2$—C≡CH | 1 | | |
| (131) | $C_3H_7$—n | $CCl_2F$ | 1 | 95 | $n_D^{28}$:1.5082 |
| (132) | $C_4H_9$—n | $CCl_3$ | 1 | | |
| (133) | $C_3H_7$—iso | $C_3H_7$—n | 1 | | |
| (134) | $CH_2$=CH—$CH_2$ | $CCl_3$ | 1 | | |
| (135) | CH≡C—$CH_2$ | $CCl_3$ | 1 | | |
| (136) |  | $CCl_2F$ | 1 | | |
| (137) |  | $CCl_2F$ | 1 | 95 | $n_D^{28}$:1.5259 |
| (138) | $C_2H_5O$—$CH_2$—$CH_2$ | $CCl_2F$ | 1 | | |
| (139) | NC—$CH_2$—$CH_2$ | $CCl_2F$ | 1 | | |
| (140) | NC—$CH_2$—$CH_2$ | $CCl_3$ | 1 | | |
| (141) | $C_2H_5O$—$CH_2$—$CH_2$ | $CCl_3$ | 1 | | |
| (142) | $C_4H_9$—tert. | $CH_3$ | 1 | | |
| (143) | $C_3H_7$—iso | $CH_3$ | 2 | | |
| (144) | $C_3H_7$—iso | 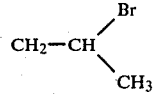 | 1 | | |
| (145) | $CH(C_2H_5)_2$ | $CCl_2F$ | 1 | | |
| (146) | $CH_3$—S—$CH_2$ | $CCl_2F$ | 1 | | |
| (147) | $CH_3$—S—$CH_2$ | $CCl_3$ | 1 | | |
| (148) | $C_4H_9$—tert. | $CH_2$—CH=$CH_2$ | 1 | | |
| (149) | $C_4H_9$—n | $CCl_2F$ | 1 | 97 | $n_D^{28}$:1.5052 |
| (150) | $C_2H_5$ | $CCl_2F$ | 1 | 93 | $n_D^{28}$:1.5130 |
| (151) | $CH_2$—$C(CH_3)_3$ | $CCl_2F$ | 1 | | |
| (152) | $C(CH_3)_2$—$CH_2$—$CH_3$ | $CCl_2F$ | 1 | 94 | $n_D^{23}$:1.5071 |
| (153) | $CH_2$=CH—$CH_2$ | $CCl_2F$ | 1 | | |
| (154) | CH≡C—$CH_2$ | $CCl_2F$ | 1 | | |
| (155) | $C_3H_7$—iso | $CClF_2$ | 1 | | |
| (156) | $C_4H_9$—tert. | $CClF_2$ | 1 | | |
| (157) | $C(CH_3)_2$—$CH_2$—$CH_3$ | $CCl_3$ | 1 | | |
| (158) | $C_3H_7$—iso | $C_3H_7$—n | 1 | | |
| (159) | $CH_3$ | $CCl_2F$ | 1 | 87 | $n_D^{28}$:1.5196 |
| (160) | $CH_2$—CH(Br)(CH_3) | $CCl_2F$ | 1 | 82 | $n_D^{19}$:1.5352 |
| (161) | $CH_2$—$CH_2$—Br | $CCl_2F$ | 1 | 88 | $n_D^{22}$:1.5416 |

The pesticidal activity of the compounds of the formula (I) is illustrated by the following examples in which each of the compounds of the present invention is identified by the number (in brackets) assigned to it in the preparative examples hereinabove:

EXAMPLE 9

Phaedon larvae test
Solvent: 3 parts by weight of dimethylformamide
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Cabbage leaves (*Brassica oleracea*) were treated by being dipped into the preparation of the active compound of the desired concentration and were infested with mustard beetle larvae (*Phaedon cochleariae*), as long as the leaves were still wet.

After the specified period of time, the destruction in % was determined. 100% meant that all the beetle larvae had been killed; 0% meant that none of the beetle larvae had been killed.

In this test, for example, the following compounds showed a superior activity compared with the prior art: (1), (4), (6), (7), (11), (14), (17), (18), (20), (22), (25), (29), (31), (33), (36), (39), (40), (50), (51), (57), (63), (67), (93), (127), (103), (128), (118), (119), (120), (106), (70), (66), (92), (77), (90), (88), (79), (75), (83), (85), (61), (107), (81) and (101).

EXAMPLE 10

Test insect: *Phorbia antiqua* maggots (in the soil)
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance, only the amount by weight of active compound per unit volume of soil, which was given in ppm (=mg/l), being decisive. The soil was filled into pots and the pots were left to stand at room temperature.

After 24 hours, the test insects were introduced into the treated soil, and after a further 2 to 7 days the degree of effectiveness of the active compound was determined in % by counting the dead and the live test insects. The degree of effectiveness was 100% if all the test insects had been killed and was 0% if just as many test insects were still alive as in the case of the untreated control.

In this test, for example, the following compounds showed a superior action compared with the prior art: (67), (50), (51), (36), (40) and (57).

EXAMPLE 11

Root-system action
Test insect: Myzus persicae
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance, only the amount by weight of active compound per unit volume of soil, which was given in ppm (=mg/l), being decisive. The treated soil was filled into pots and these were planted with cabbage (*Brassica oleracea*). The active compound could in this way be taken up from the soil by the roots of the plants and be transported into the leaves.

To demonstrate the root-systemic effect, exclusively the leaves were infested with the abovementioned test insects after 7 days. After a further 2 days, the evaluation is made by counting or estimating the dead insects. The root-systemic action of the active compound was deduced from the mortality figures. It was 100% if all the test insects had been killed and 0% if just as many test insects were still alive as in the case of the untreated control.

In this test, for example, the following compounds showed a superior action compared with the prior art: (67), (50), (51), (36), (40), (57) and (115).

EXAMPLE 12

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance, only the amount of active compound per unit volume of soil, which was given in ppm, being decisive. The treated soil was filled into pots, lettuce was sown in and the pots were kept at a greenhouse temperature of 27° C.

After four weeks, the lettuce roots were examined for infestation with nematodes (root galls), and the degree of effectiveness of the active compound was determined in %. The degree of effectiveness was 100% if infestation was completely avoided and was 0% if the infestation was just as high as in the case of the control plants in untreated soil which had been infested in the same manner.

In this test, for example, the following compound showed a superior activity compared with the prior art: (67).

EXAMPLE 13

$LT_{100}$ test for Diptera
Test insects: Aedes aegypti
Number of test animals: 25
Solvent: Acetone The active compound was taken up in the solvent at a rate of 2 g per 1000 ml. The solution thus obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per $m^2$ of filter paper varied with the concentration of the solution of active compound used. The stated number of test insects was then placed in the Petri dish and the dish was covered with a glass lid.

The condition of the test insects was continuously checked. The time which was necessary for a 100% knockdown effect was determined.

In this test, for example, the following compounds showed a superior action compared with the prior art: (14), (33), (31), (25), (17), (115), (11), (20), (39), (51), (29), (36), (10), (7), (18), (40), (57), (67) and (50).

It will be appreciated that the instant specification and examples are set forth by way of illustration and not limitation, and that various modifications and changes may be made without departing from the spirit and scope of the present invention.

What is claimed is:

1. An N-acylated N-methyl-carbamic acid 0-pyrazol-4-yl ester of the formula

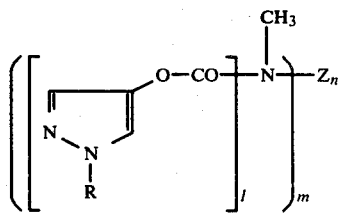

in which

R represents $C_1$-$C_5$-alkyl which is optionally substituted by halogen, cyano, $C_1$-$C_4$-alkoxy or $C_1$-$C_4$-alkylthio, or represents $C_3$-$C_5$ alkenyl, $C_3$-$C_5$-alkynyl or $C_3$-$C_6$-cycloalkyl, or represents an optionally halogen-substituted phenyl, benzyl or phenylethyl radical, Z represents the radical $-S_r(O)_sR^4$, r represents 1 or 2, s represents zero, 1 or 2, and $R^4$ represents optionally halogen-substituted $C_1$-$C_4$-alkyl, $C_3$-$C_5$-alkenyl, $C_3$-$C_5$-alkynyl or $C_3$-$C_6$-cycloalkyl, or represents a phenyl, benzyl or phenylethyl radical which is optionally substituted by halogen, cyano, nitro, trifluoromethyl, $C_1$-$C_4$-alkyl or $C_1$-$C_4$-alkoxy, when each of l, m and n represents 1; or Z represents sulfur when l is 1, m is 2 and n is 1; and when n represents zero, l is 2 and m is 1.

2. A compound according to claim 1 of the formula

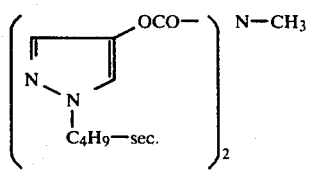

3. A compound according to claim 1 of the formula

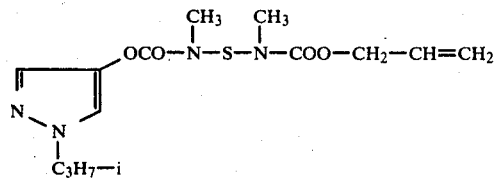

4. A compound according to claim 1 of the formula

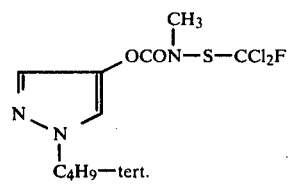

5. A compound according to claim 1 of the formula

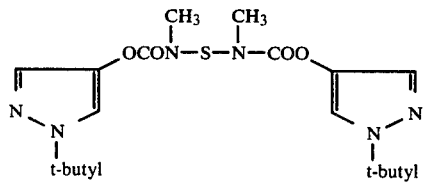

6. A pesticidal composition comprising a pesticidally effective amount of a compound according to claim 1 in admixture with a diluent.

7. A method of combating pests comprising applying to the pests, or to a habitat thereof, a pesticidally effective amount of a compound according to claim 1.

8. The method according to claim 7, in which said compound is

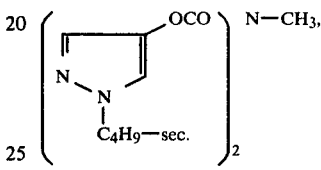

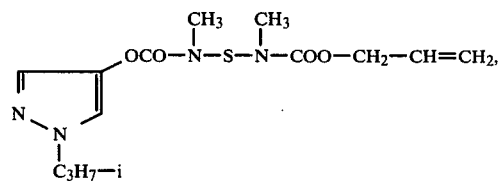

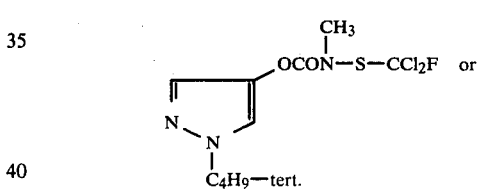

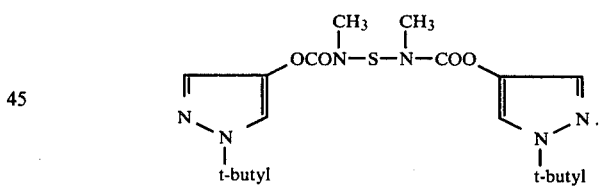

9. A compound of the formula

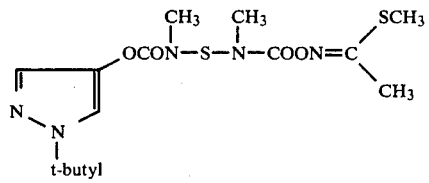

10. A pesticidal composition comprising a pesticidally effective amount of a compound according to claim 9 in admixture with a diluent.

11. A method of combating pests comprising applying to the pests, or to a habitat thereof, a pesticidally effective amount of a compound according to claim 9.

* * * * *